United States Patent [19]

Znaiden et al.

[11] Patent Number: 5,556,630
[45] Date of Patent: Sep. 17, 1996

[54] COLD CREAMS CONTAINING ACYL LACTYLATES

[75] Inventors: Alexander P. Znaiden, Trumbull; Susan C. Wivell, Madison; Virginia R. Kickertz, Stratford, all of Conn.

[73] Assignee: Chesebrough-Pond's USC Co., Division of Conopco, Inc., Greenwich, Conn.

[21] Appl. No.: 427,787

[22] Filed: Apr. 25, 1995

Related U.S. Application Data

[63] Continuation-in-part of Ser. No. 367,658, Jan. 3, 1995, abandoned.

[51] Int. Cl.$^6$ ..................................................... A61K 7/48
[52] U.S. Cl. ........................ 424/401; 514/844; 514/846
[58] Field of Search ..................................... 514/844, 846; 424/401

[56] References Cited

U.S. PATENT DOCUMENTS

| | | | |
|---|---|---|---|
| 3,098,795 | 7/1963 | Kreps | 167/90 |
| 3,472,940 | 10/1969 | Osipow et al. | 424/365 |
| 3,728,447 | 4/1973 | Osipow et al. | 424/70 |
| 4,184,978 | 1/1980 | France et al. | 252/309 |
| 4,198,311 | 4/1980 | France et al. | 252/117 |
| 4,800,076 | 1/1989 | Bhat | 424/69 |
| 4,946,832 | 8/1990 | Goode et al. | 514/53 |
| 5,139,781 | 8/1992 | Birtwistle et al. | 424/401 |

FOREIGN PATENT DOCUMENTS

| | | |
|---|---|---|
| 0194097 | 9/1986 | European Pat. Off. . |
| 0278370 | 8/1988 | European Pat. Off. . |
| 0442708 | 8/1991 | European Pat. Off. . |
| WO88/06880 | 9/1988 | WIPO . |

OTHER PUBLICATIONS

Chemical Abstracts vol. 110, 1989, p. 390.
Baiocchi et al. "Use of acyl lactylates in cosmetics and toiletries" Cosmetics and Perfumery 90, pp. 31–34 (1975).
Osipow et al. "Fatty Acid Lactylates" Drug Cosmet. Ind., May 1969, 64 ff.
L. J. Murphy, "Sorption of acyl lactylates by hair and skin as documented by radio tracer studies" Cosmetics and Toiletries 94, 43 ff. (1979).
Serna–Saldivar et al., "Effect of Sodium Stearoyl –2–2Lactylate on the Rheological and Baking Properties of Wheat Bread Fortified with Defeated Soybean and Sesame Meal" Journal of Food Science, vol. 53, No. 1 (1988), pp. 211–214, 230.

*Primary Examiner*—C. Warren Ivy
*Assistant Examiner*—Evelyn Huang
*Attorney, Agent, or Firm*—Milton L. Honig

[57] ABSTRACT

A cold cream cosmetic composition is provided that includes a wax, mineral oil, and a $C_{18}$–$C_{30}$ acyl lactylate salt. These compositions feel drier on the skin and are more water-rinsable than traditional cold cream.

7 Claims, No Drawings

5,556,630

COLD CREAMS CONTAINING ACYL LACTYLATES

This is a continuation-in-part application of Ser. No. 08/367,658 filed Jan. 3, 1995 abandoned.

BACKGROUND OF THE INVENTION

1. Field of the Invention

The invention concerns cold cream cosmetics with improved water rinsability and drier feel than traditional cold creams.

2. The Related Art

Modern cleansing creams are based on the solvent action of mineral oil to remove through binding either grime or make-up from skin. Removal of pigments of rouge, lipstick and face powder is a daily problem for most women. Cleansing creams have proved the ideal agent to perform this function.

Historically cleansing creams evolved over a period of centuries. Galen, a Greek physician around the year 150, is reported to be the inventor of the first cold cream. Skin preparations of that period consisted of animal and vegetable fats and oils. Beeswax and olive oil were the prime ingredients. Galen conceived the idea of incorporating water into a molten mixture of beeswax and olive oils. In the resultant product, the emollient effect of oil was accelerated, and a pleasant cooling effect was obtained from evaporation of water. Unfortunately the process of manufacture was slow and laborious. Products were also unstable and subject to developing rancidity. In time, sweet almond oil replaced the olive oil of the older formulations. Borax was introduced to cut manufacturing time, and a whiter and more stable emulsion resulted.

A cold cream can be classified as a form of cleansing cream but with a heavier body. There is even a monograph for "cold cream" in the USP which describes its components as wax, mineral oil, water and sodium borate.

New cleansing chemicals and formulations have been developed over the last several decades that have provided technical advantage over traditional cold cream. These new products have lured away customers who seek less oily and better water rinsability properties.

Accordingly, it is an object of the present invention to provide a cosmetic composition with a less heavy, less greasy skinfeel than traditional cold creams.

It is another object of the present invention to provide a cosmetic composition having better water rinsability than that of traditional cold cream.

Still a further object of the present invention is to provide a cosmetic composition in emulsion form having stability no less than that of traditional cold cream even though containing potentially destabilizing additives such as α-hydroxy acids or their precursors.

These and other objects of the present invention will become more apparent through the following summary and detailed description.

SUMMARY OF THE INVENTION

A cold cream cosmetic composition is provided that includes:

(i) from about 10 to about 50% by weight of water;

(ii) from about 5 to about 40% by weight of a wax;

(iii) from about 10 to about 80% by weight of mineral oil; and (iv) from about 0.01 to about 20% by weight of a $C_{18}$–$C_{30}$ acyl lactylate salt.

DETAILED DESCRIPTION OF THE INVENTION

Now it has been discovered that $C_{18}$-$C_{30}$ acyl lactylates can substantially improve cold cream formulations. Acyl lactylates provide products having a richer, creamier feel. On the skin, the product is observed to be less oily or drier, but very smooth and soft. Furthermore, spontaneous emulsification with water was observed with the cold creams containing acyl lactylates. This was unusual in that cold cream, being less than 50% aqueous, normally does not blend well with water and forms a greasy film on the skin. Soap with warm water or an alcoholic astringent is usually needed to remove traditional cold cream residues left behind after tissuing. Typical surfactant materials other than lactylates were found to impart a blooming or rinsing effect not compatible with these wax-containing products.

Accordingly, an essential element of the present invention is that of a $C_{18}$–$C_{30}$, especially $C_{20}$–$C_{30}$, acyl lactylate salt. Most preferred is behenoyl lactylate salt, especially sodium behenoyl lactylate. Other suitable cations to form the lactylate salt are the alkali metal, alkaline earth metal, ammonium and $C_2$–$C_{12}$ alkanolammonium cations. Acyl lactylate salts are commercially available from the C. J. Patterson Division of RITA Corporation. Amounts of the acyl lactylate salts will range from about 0.01 to about 20%, preferably from about 0.5 to about 10%, optimally from about 2 to about 5% by weight.

Mineral oil is another important element in the cosmetic compositions of the present invention. Amounts of mineral oil may range from about 10 to about 80%, preferably from about 25 to about 60%, optimally from about 40 to about 50% by weight.

Wax is yet another important element of compositions according to the present invention. Among suitable waxes are beeswax, ceresin, spermaceti, carnauba, ozokerite, candelilla and mixtures of these waxes. Particularly preferred are combinations of beeswax and ceresin in weight ratios of about 5:1 to about 1:5, preferably about 2:1 to about 1:1. Amounts of total wax may range from about 0.5 to about 40%, preferably from about 1 to about 20%, optimally from about 20 to about 10% by weight.

Water is a further important element of compositions according to the present invention. Amounts of water may range from about 10 to about 50%, preferably from about 15 to about 35%, optimally from about 20 to about 30% by weight.

An alkali agent can optionally be incorporated as an element of cosmetic compositions according to the present invention. Illustrative alkali agents are $C_2$-$C_{10}$ alkanolamines (e.g. triethanolamine), sodium hydroxide, potassium hydroxide, ammonium hydroxide and borate salts. Sodium borate is most preferred, being available as borax in various states of hydration including anhydrous borax, borax decahydrate and borax pentahydrate. Amounts of the alkali agent may range from 0.01 to about 5%, preferably from about 0.5 to about 3%, optimally from about 1 to about 2% by weight.

Thickeners/viscosifiers may optionally be found in compositions to the present invention. Suitable thickeners include xanthan gum, sodium carboxymethyl cellulose, hydroxyalkyl and alkyl cellulose, and cross-linked acrylic acid polymers such as those sold by B. F. Goodrich under the Carbopol trademark (Carbomer, according to CTFA nomenclature). Most preferred is Carbopol 934®. Amounts of the thickeners/viscosifiers may range from about 0.01 to about 10%, preferably from about 0.1 to about 1% by weight.

Preservatives can also be incorporated in amounts effective to protect against growth of potentially harmful microorganism in cosmetic compositions according to the present invention. Levels of such preservatives may range from about 0.001 to about 1% by weight. Illustrative preservatives are methyl paraben, propyl paraben, imidazolidinyl urea, sodium dehydroxyacetate and benzyl alcohol. Other minor adjunct ingredients may also be included such as fragrances, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A clinical study was conducted among a group of twenty panelists selected as being non-cold cream users. These panelists were provided with a commercial cold cream (Formula A) and the same commercial product including 4% sodium behenoyl lactylate (Formula B). These formulas are outlined in Table I.

TABLE I

| INGREDIENT | FORMULA (WT. %) | |
| --- | --- | --- |
| | A | B |
| Mineral Oil | 47.2 | 47.2 |
| Beeswax | 9.3 | 7.3 |
| Ceresin Wax | 6.0 | 4.0 |
| Sodium Behenoyl Lactylate | 0 | 4.0 |
| Carbopol 934 ® (2% Aqueous) | 10.0 | 10.0 |
| Borax | 1.7 | 1.7 |
| Fragrance | 0.2 | 0.2 |
| Water | to 100 | to 100 |

After the panelists used both products, they were requested to compare Formulas A and B according to the following attributes on a preference basis.

TABLE II

| ATTRIBUTE | PANEL TEST RESULTS | | |
| --- | --- | --- | --- |
| | FORMULA A PREFERRED | FORMULA B PREFERRED | NO PREFERENCE |
| Being Easy To Use | 4 | 8 | 8 |
| Product Goes On Smoothly | 12 | 4 | 4 |
| Removing Dirt & Oils From Skin | 4 | 12 | 4 |
| Being An Effective Cleanser | 4 | 12 | 4 |
| Removing Eye Make-Up Easily | 4 | 12 | 4 |
| Removing Facial Make-Up Easily | 4 | 12 | 4 |
| Removing Eye Make-Up Completely | 4 | 12 | 4 |
| Feeling Light On The Skin | 8 | 4 | 8 |
| Non-Irritating To Skin | 8 | 8 | 4 |
| Non-Irritating To Eyes | 8 | 8 | 4 |
| Leaving Skin Feeling Soft/Smooth | 4 | 12 | 4 |
| Gentle Enough To Use Around Eyes | 4 | 8 | 8 |
| Rinsing Well With Water | 4 | 8 | 8 |
| Having A Pleasant Scent | 8 | 4 | 8 |
| Deep Cleaning Pores | 4 | 12 | 4 |
| Wiping Off Easily | 8 | 4 | 8 |
| Not Leaving Skin Feeling Dry | 8 | 8 | 4 |
| No Greasy Residue | 4 | 8 | 8 |
| No Oily Residue | 4 | 8 | 8 |
| Leaving Skin Feeling Clean | 4 | 8 | 8 |
| Cleansing Quickly | 4 | 8 | 8 |

From Table II it is seen that Formula B with behenoyl lactylate is strongly preferred in several categories, and only a few categories is it inferior to the traditional cold cream Formula A. The highly preferred categories were that of removing dirt/oils, effective cleanser, removing eye make-up easily, removing facial make-up easily, removing eye make-up completely, leaving skin feeling soft/smooth and deep cleaning of pores.

EXAMPLE 2

A set of formulations were prepared to evaluate performance of different chain length acyl lactylates. The following base cold cream was prepared and various lactylates were incorporated therein at 4% by weight. These were compared to a control without lactylate but having 2% more of both beeswax and ceresin wax than the base cold cream formula.

TABLE III

Base Cold Cream Formula

| INGREDIENT | WEIGHT % |
|---|---|
| Mineral Oil | 47.2 |
| Beeswax | 7.3 |
| Ceresin Wax | 4.0 |
| Lactylate Salt | 4.0 |
| Carbopol 934 ® (2% Aqueous) | 10.0 |
| Borax | 1.7 |
| Fragrance | 0.2 |
| Water | to 100 |

TABLE IV

Stability Profile and Physical Properties

| PRODUCT | | RT/22° C. | 37° C. | 43° C. | 50° C. |
|---|---|---|---|---|---|
| No Lactylate (Control) | form | cream | same | same | same |
| | skinfeel | greasy, not rinsable | same | same | same |
| Behenoyl Lactylate (C22) | form | cream (harder) | same | same | same |
| | skinfeel | less greasy, rinsable | same | same | same |
| Isostearoyl Lactylate (C18) | form | cream (soft) | same | same | significant phase separation after 1 mo. |
| | skinfeel | greasy, not rinsable | same | same | |
| Lauroyl Lactylate (C12) | form | thin lotion | n/a | n/a | n/a |
| | skinfeel | greasy, not rinsable | n/a | n/a | n/a |

From the results in Table IV it is evident that only the behenoyl lactylate formulation is rinsable in contrast to the control and to those with isostearoyl and lauroyl lactylate. Furthermore, the behenoyl lactylate formulation is less greasy than all of the others tested and has a hardness much closer to the control formula than the formulations incorporating any of the other lactylates.

EXAMPLE 3

A further formulation of a borax-free cold cream is hereunder illustrated. The formula are outlined in Table V.

| INGREDIENT | FORMULA (WT. %) | | | |
|---|---|---|---|---|
| | G | E | F | H |
| Mineral Oil | 35.2 | 46.0 | 48.2 | 49.0 |
| Sodium Behenoyl Lactylate | 6.0 | 6.0 | 4.0 | 5.0 |
| Beeswax | 3.5 | 2.0 | 1.0 | 2.0 |
| Caresin Wax | 2.0 | 1.5 | 0.9 | 2.0 |
| Carbopol 934 (2% Aqueous) | 5.0 | 5.0 | 5.0 | 5.0 |
| Butylene Glycol | 3.0 | 4.0 | 4.0 | 4.5 |
| PEG-100 Stearate | 1.5 | 1.5 | 1.8 | 1.8 |
| Petrolatum (2.5 Soft) | 1.0 | 1.0 | 1.0 | 1.0 |
| Glycerin | 0.9 | 1.3 | 1.0 | 1.0 |
| Sorbitan Sesquioleate | 0.9 | 0.8 | 1.0 | 0.9 |
| Glyceral Stearate | 0.5 | 0.7 | 1.0 | 0.5 |
| Cetyl Alcohol | 0.3 | 0.3 | 0.3 | 0.3 |
| Stearic Acid | 0.3 | 0.3 | 0.3 | 0.3 |
| Fragrance | 0.2 | 0.2 | 0.2 | 0.2 |
| Dimethicone | 0.1 | 0.1 | 0.1 | 0.1 |
| Triethanolamine | 0.1 | 0.1 | 0.1 | 0.1 |
| Glydant Plus ® | 0.1 | 0.1 | 0.1 | 0.1 |
| Glycolic Acid | 0.02 | 0.02 | 0.02 | 0.02 |
| Vitamin E Acetate | 0.01 | 0.01 | 0.01 | 0.01 |
| Ascorbyl Palmitate | 0.01 | 0.01 | 0.01 | 0.01 |
| Hydroxycaprylic Acid | 0.01 | 0.01 | 0.01 | 0.01 |
| Water | to 100 | to 100 | to 100 | to 100 |

The foregoing description and Examples illustrate selected embodiments of the present invention. In light thereof, various modifications will be suggested to one skilled in the art, all of which are in the spirit and purview of this invention.

What is claimed is:

1. A cold cream cosmetic composition comprising:
   (i) from about 10 to about 50% by weight of water;
   (ii) from about 0.5 to about 40% by weight of a wax;
   (iii) from about 10 to about 80% by weight of mineral oil;
   (iv) from about 0.01 to about 20% by weight of a behenoyl lactylate salt.

2. A composition according to claim 1 wherein the behenoyl lactylate salt is present in an amount from about 0.5 to about 10% by weight.

3. A composition according to claim 1 further comprising an alkali agent selected from the group consisting of $C_2$–$C_{10}$ alkanolamine, sodium hydroxide, potassium hydroxide and borate salts.

4. A composition according to claim 3 wherein the alkali agent is a borate salt.

5. A composition according to claim 1 wherein the mineral oil is present in an amount from about 25 to about 60% by weight.

6. A composition according to claim 1 wherein the wax is selected from the group consisting of beeswax, ceresin, spermaceti, carnauba, ozokerite, candelilla and mixtures thereof.

7. A composition according to claim 1 wherein the wax is a mixture of beeswax and ceresin wax in a weight ratio of about 5:1 to about 1:5.

* * * * *